(12) United States Patent
Tanaka et al.

(10) Patent No.: US 7,916,990 B2
(45) Date of Patent: Mar. 29, 2011

(54) OPTICAL FIBER BUNDLE AND METHOD OF MANUFACTURING THE SAME

(75) Inventors: Toshio Tanaka, Hino (JP); Noboru Yamada, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 389 days.

(21) Appl. No.: 11/952,454

(22) Filed: Dec. 7, 2007

(65) Prior Publication Data

US 2008/0118212 A1 May 22, 2008

Related U.S. Application Data

(63) Continuation of application No. PCT/JP2006/310548, filed on May 26, 2006.

(30) Foreign Application Priority Data

Jun. 7, 2005 (JP) ................................. 2005-166877

(51) Int. Cl.
*G02B 6/06* (2006.01)
*A61B 1/07* (2006.01)
(52) U.S. Cl. ....................................... 385/117; 600/182
(58) Field of Classification Search .................. 385/117; 600/182

See application file for complete search history.

(56) References Cited

U.S. PATENT DOCUMENTS

| | | | | |
|---|---|---|---|---|
| 3,089,484 A | * | 5/1963 | Hett | 600/139 |
| 4,969,705 A | * | 11/1990 | Stoy et al. | 385/96 |
| 5,426,474 A | | 6/1995 | Rubtsov et al. | |
| 6,144,791 A | | 11/2000 | Wach et al. | |
| 2003/0169972 A1 | * | 9/2003 | Stanton | 385/54 |

FOREIGN PATENT DOCUMENTS

GB  2 283 105 A  4/1995

* cited by examiner

*Primary Examiner* — Jerry T Rahll
(74) *Attorney, Agent, or Firm* — Scully, Scott, Murphy & Presser, P.C.

(57) ABSTRACT

A plurality of optical fibers are bundled, and the fiber bundle is cut at a part of a mouthpiece which is fixed on an intermediate part of the fiber bundle. Thus, the fiber bundle is divided into a first optical fiber bundle and a second optical fiber bundle. Division surfaces of the first and second optical fiber bundles have the same properties and condition since the first and second optical fiber bundles are formed of the fiber bundle that is obtained by bundling the same optical fibers. The first optical fiber bundle is assembled in an insertion section of an endoscope and the second optical fiber bundle is assembled in a flexible tube, and a first light guide in the insertion section of the endoscope and a second light guide in the flexible tube are formed. Thereby, a separable light transmission path of the light guide is formed.

3 Claims, 8 Drawing Sheets

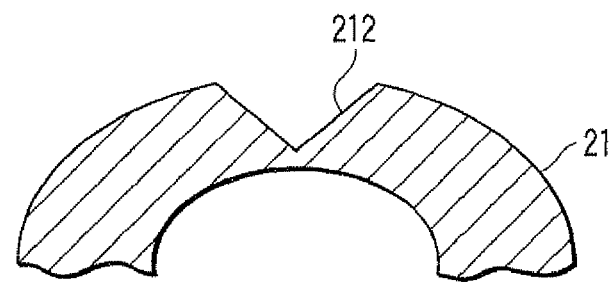
F I G. 16
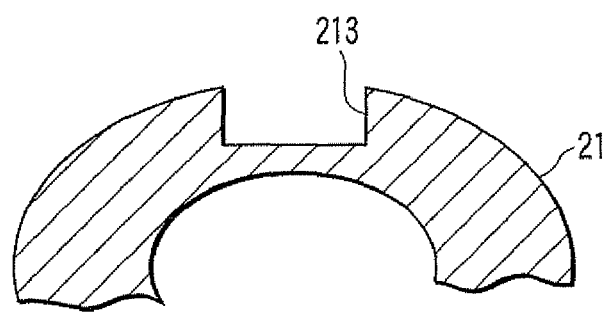
F I G. 17
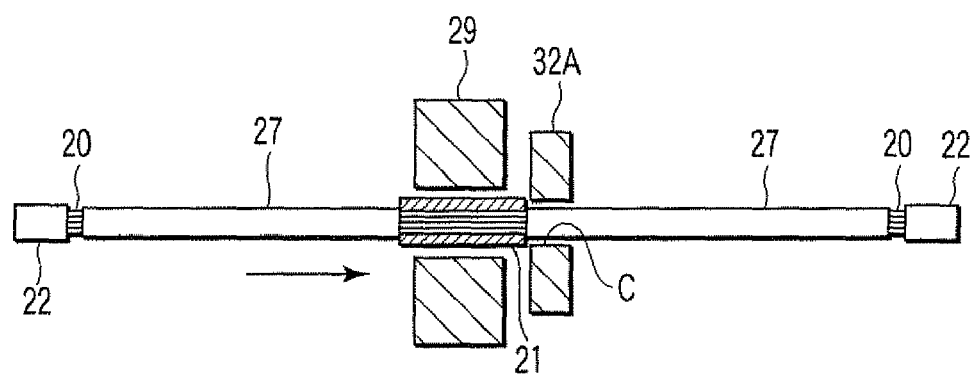
F I G. 18

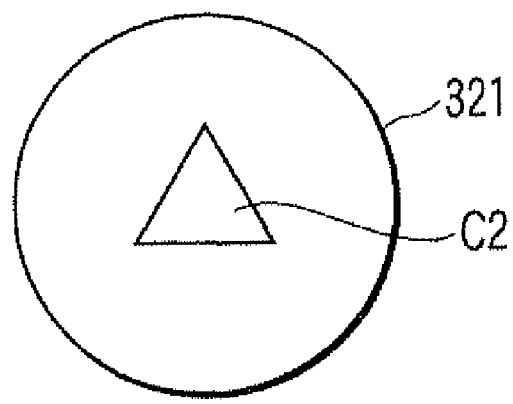
F I G. 22
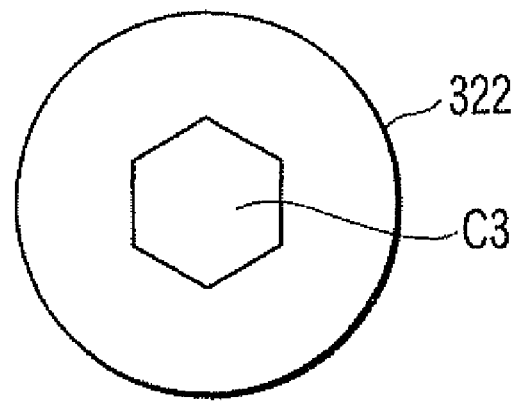
F I G. 23

OPTICAL FIBER BUNDLE AND METHOD OF MANUFACTURING THE SAME

CROSS-REFERENCE TO RELATED APPLICATIONS

This is a Continuation Application of PCT Application No. PCT/JP2006/310548, filed May 26, 2006, which was published under PCT Article 21(2) in Japanese.

This application is based upon and claims the benefit of priority from prior Japanese Patent Application No. 2005-166877 filed Jun. 7, 2005, the entire contents of which are incorporated herein by reference.

BACKGROUND OF THE INVENTION

1. Field of the Invention

The present invention relates to an optical fiber bundle which is used, for example, in a light guide provided in an endoscope, an optical fiber sensor, etc., and a method of manufacturing the optical fiber bundle.

2. Description of the Related Art

In general, in a main body of an endoscope, an operation section is coupled to a proximal end portion of an elongated insertion section that is to be inserted into the human body. An image guide and a light guide for illuminating an object of observation are inserted in the insertion section. Further, one end portion of a flexible tube, such as a light guide cable, is connected to the operation section. The light guide is extended from within the insertion section to the flexible tube side. The other end portion of the flexible tube is connected to an external light source. Illumination light from the external light source is supplied to the light guide, and the object of observation is illuminated.

In the meantime, in order to enhance the functionality of the endoscope, there is a demand for separation between the operation section of the endoscope and the flexible tube such as a light guide cable. In this case, the operation section of the endoscope is provided with a flexible tube connection section to which the flexible tube is detachably attached. Further, the flexible tube is provided with an endoscope connection section. The endoscope connection section of the flexible tube is detachably attached to the flexible tube connection section of the operation section.

As described above, in the case where the operation section of the endoscope is separated from the flexible tube such as a light guide cable, it is necessary, in the prior art, to cut a single light guide, which extends from within the insertion section to the flexible tube side, and to separate the single light guide into a light guide on the insertion section side and a light guide on the flexible tube side. In addition, at the connection part between the flexible tube connection section of the operation section and the endoscope connection section of the flexible tube, the end face of the light guide on the flexible tube side and the end face of the light guide on the endoscope body side are configured to be optically coupled. By this structure, illumination light, which is guided from the light guide on the flexible tube side, is transmitted to the light guide on the endoscope body side so that the object of observation may be illuminated, and the functionality of the endoscope is secured.

Besides, the optical fiber bundle that constitutes the light guide is conventionally manufactured by the following method. Specifically, end portions of a plurality of optical fibers are bundled with use of a glass tube, and these end portions are fused. Thereby, the end face of the light guide connection section is formed (see, e.g. Jpn. Pat. Appln. KOKAI Publication No. 6-347645). The optical fiber bundles that are manufactured in this manner are assembled in the state in which the optical fiber bundles are inserted in the insertion section and the flexible tube.

When the insertion section of the endoscope body and the flexible tube are connected, the end face of the light guide of the flexible tube is optically coupled to the end face of the light guide of the endoscope body. Thereby, illumination light from the external light source is guided from the optical fiber bundle of the light guide on the flexible tube side to the optical fiber bundle of the light guide on the insertion section side, and the illumination light is radiated on the object of observation.

BRIEF SUMMARY OF THE INVENTION

In the above-described conventional method of manufacturing the optical fiber bundle, the end portion of the optical fiber bundle is bundled by using the glass tube, the end portion is fused, and the end faces of the light guide connection parts are individually formed. Thus, the end-face properties and condition of the light guide vary between optical fiber bundles that are manufactured, and it is difficult to form all products with uniform end-face properties and condition. Thus, in the conventional optical fiber bundle manufacturing method, since the end-face properties and condition of the light guide of the flexible tube are different from those of the light guide of the endoscope body, illumination light is not effectively transmitted at the light guide connection part between the end face of the light guide of the flexible tube and the end face of the light guide of the endoscope body, and the loss of light increases. For example, when light from an external light source is transmitted, if the light amount is 100% in the case where the light transmission path is formed of a single light guide, the light amount at the time of illumination decreases to about 60% in the case where two light guides are connected, owing to the difference in properties and condition between the end faces of the optical fiber bundles of the respective light guides. Thus, there is such a serious problem that the loss of illumination light is very large, namely, 40%.

The present invention has been made in consideration of the above circumstances, and the object of the invention is to provide an optical fiber bundle and a manufacturing method thereof, which can realize high-efficiency light transmission characteristics and separation/connection of a light transmission path with simple structure.

An optical fiber bundle according to an aspect of the invention wherein an intermediate part of a fiber bundle, which is formed by bundling a plurality of optical fibers, is provided with a fixing section which fixes the optical fibers, and the fiber bundle is cut at a part of the fixing section in a direction perpendicular to an axial direction of the fiber bundle, and divided into a pair of divisional fiber bundles, and division surfaces of the divisional fiber bundles are disposed to be opposed to each other, thereby forming a connectable/separable light transmission path for optical coupling.

According to the above structure, a pair of divisional fiber bundles are formed by cutting and dividing a fiber bundle of a plurality of optical fibers at a fixing part on an intermediate part of the fiber bundle in a direction perpendicular to the axial direction of the fiber bundle. Thereby, the division surfaces have the same properties and condition. Therefore, even in the case where the pair of divisional fiber bundles are detachably disposed such that their division surfaces are opposed to each other, the loss of light amount between the divisional fiber bundles in the coupled state at the time of light transmission can be minimized. As a result, the separable light transmission path can be formed with high efficiency.

Preferably, the fixing section has a cylindrical bundling member which is mounted on an outer peripheral surface of the fiber bundle, and the pair of divisional fiber bundles have division surfaces which are formed by cutting the fiber bundle at a part of the bundling member in the direction perpendicular to the axial direction of the fiber bundle.

Preferably, the bundling member has alignment means for aligning a rotational position in a direction about the axis of the fiber bundle, in accordance with at least a division part of the pair of divisional fiber bundles.

Preferably, the alignment means includes at least one of a mark line, a V groove and a U groove, which are axially provided in a straight shape and extend over the division surfaces on an outer peripheral part of the bundling member.

An optical fiber bundle in another aspect of the present invention which is assembled in an endoscope, comprising: an insertion section in which a first light guide is provided; an operation section coupled to a proximal end portion of the insertion section; a light guide cable connection section which is provided on the operation section and to which an external light guide cable is connected; and a light guide cable in which a second light guide is provided and includes, at one end portion thereof, an external light source connection section that is connected to an external light source, and includes, at the other end portion thereof, an endoscope connection section that is detachably connected to the light guide cable connection section, wherein the optical fiber bundle includes: a fixing section which fixes a plurality of optical fibers and is provided at an intermediate part of a fiber bundle which is formed by bundling the plurality of optical fibers; and a pair of divisional fiber bundles which are formed by cutting the fiber bundle at a part of the fixing section in a direction perpendicular to an axial direction of the fiber bundle, a first divisional fiber bundle, which is formed of one of the divisional fiber bundles, is assembled in the insertion section, thereby forming the first light guide, a division surface of the first divisional fiber bundle is disposed at the light guide cable connection section, a second divisional fiber bundle, which is formed of the other divisional fiber bundle, is assembled in the light guide cable, thereby forming the second light guide, a division surface of the second divisional fiber bundle is disposed at the endoscope connection section, and the division surface of the first divisional fiber bundle and the division surface of the second divisional fiber bundle are disposed to be opposed to each other when the light guide cable connection section and the endoscope connection section are connected, thereby forming a connectable/separable light transmission path for optical coupling.

A method of manufacturing an optical fiber bundle according to an aspect of the invention, comprising: an optical fiber fixing step of providing a fixing section, which fixes a plurality of optical fibers, at an intermediate part of a fiber bundle which is formed by bundling the plurality of optical fibers; a divisional fiber bundle forming step of forming a pair of divisional fiber bundles by cutting the fiber bundle at a part of the fixing section in a direction perpendicular to an axial direction of the fiber bundle; and a light transmission path forming step of forming a connectable/separable light transmission path for optical coupling, by disposing division surfaces of the pair of divisional fiber bundles such that the division surfaces are opposed to each other.

A method of manufacturing an optical fiber bundle in another aspect of the present invention, comprising: a pre-process step of fitting a cylindrical bundling member, by insertion, on an intermediate part of a fiber bundle that is formed by bundling a plurality of optical fibers, and attaching fiber bundle fixing members on both end portions of the optical fiber bundle; an immersion step of immersing the optical fiber bundle, on which the fiber bundle fixing members are attached, in ethanol in a process container which stores ethanol; a fiber bundle forming step of stretching the optical fiber bundle in a state in which the optical fiber bundle is immersed in the ethanol in the process container, and positioning the bundling member at a division part of the optical fiber bundle; a drying step of taking out the optical fiber bundle from the process container, and drying the optical fiber bundle; a fiber bundle cutting step of fixing the bundling member, which is fitted on the optical fiber bundler to the optical fiber bundle, and cutting the fiber bundle at a part of the bundling member in a direction perpendicular to an axial direction of the fiber bundle; and a divisional fiber bundle forming step of separating the fiber bundle fixing members from a pair of divisional fiber bundles which are cut at the part of the bundling member, and attaching cylindrical fixing members on end portions of the divisional fiber bundles from which the fiber bundle fixing members are separated, thus forming a pair of divisional fiber bundles.

The present invention can provide an optical fiber bundle and a manufacturing method thereof, which can realize high-efficiency light transmission characteristics and separation/connection of a light transmission path with simple structure.

BRIEF DESCRIPTION OF THE SEVERAL VIEWS OF THE DRAWING

FIG. 16 shows a main part of an optical fiber bundle according to a third embodiment of the invention;

FIG. 17 shows a main part of an optical fiber bundle according to a fourth embodiment of the invention;

FIG. 18 is a view for explaining a mouthpiece fixing work for an optical fiber bundle according to a fifth embodiment of the invention;

FIG. 22 is a view showing a diameter-reducing die which is used in order to manufacture an optical fiber bundle according to a sixth embodiment of the invention; and FIG. 23 is a view showing a diameter-reducing die which is used in order to manufacture an optical fiber bundle according to a seventh embodiment of the invention.

DETAILED DESCRIPTION OF THE INVENTION

Figure 1:
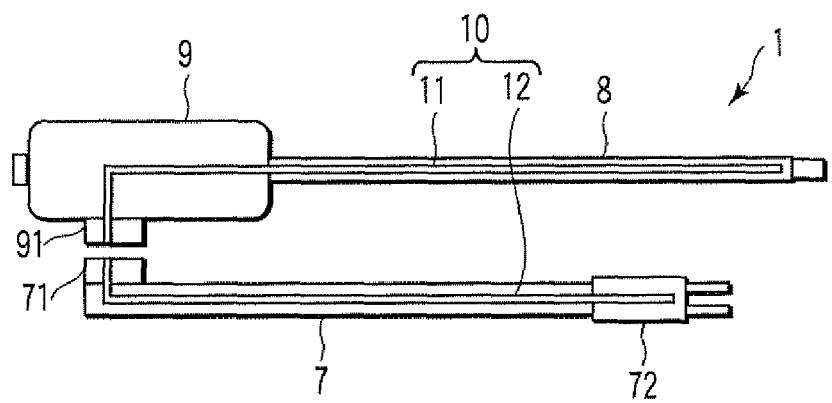
FIG. 1 schematically shows the structure of an endoscope system to which an optical fiber bundle according to a first embodiment of the present invention is applied.

An optical fiber bundle according to an embodiment of the invention and a method of manufacturing the optical fiber bundle will now be described in detail with reference to the accompanying drawings. FIG. 1 schematically shows the structure of an endoscope system in which an optical fiber bundle according to a first embodiment of the present invention is assembled. The optical fiber bundle is used as a light guide which constitutes, for example, an illumination system of an endoscope system.

In an endoscope 1 according to the present embodiment, an operation section 9 is coupled to a proximal end portion of an elongated insertion section 8 which is to be inserted in the human body. The operation section 9 is provided with a flexible tube connection section (light guide cable connection section) 91 to which an elongated flexible tube 7, such as a light guide cable, is detachably attached. Further, an endoscope connection section (optical connection section) 71 is provided on one end portion of the flexible tube 7. The endoscope connection section 71 of the flexible tube 7 is detachably attached to the flexible tube connection section 91 of the operation section 9. An external connection section 72, which is connected to an external light source (not shown), is provided at the other end portion of the elongated flexible tube 7.

A first optical fiber bundle (first divisional fiber bundle) 11, which is a first light guide, is provided in the insertion section 8. A distal end portion of the first optical fiber bundle 11 is extended to a distal end portion of the insertion section 8, and is disposed to be opposed to an illumination lens (not shown). A proximal end portion of the first optical fiber bundle 11 is coupled to the flexible tube connection section 91 of the operation section 9.

In addition, a second optical fiber bundle (second divisional fiber bundle) 12, which is a second light guide, is provided in the flexible tube 7. One end portion of the second optical fiber bundle 12 is connected to the endoscope connection section 71, and the other end portion thereof is connected to the external connection section 72. At the connection part between the flexible tube connection section 91 of the operation section 9 and the endoscope connection section 71 of the flexible tube 7, the end face of the second optical fiber bundle 12 on the flexible tube 7 side and the end face of the first optical fiber bundle 11 on the operation section 9 side are configured to be optically coupled.

Figure 2:
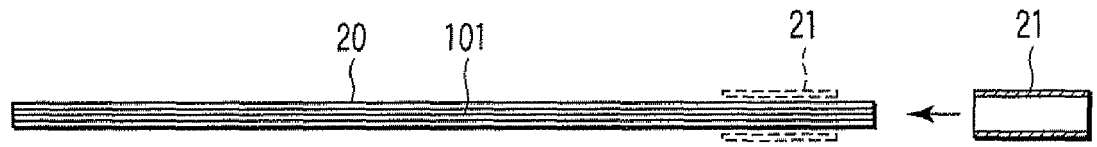
FIG. 2 is an explanatory view for explaining a work for inserting a terminal end portion of a fiber bundle into a mouthpiece in a pre-process step of a method of manufacturing the optical fiber bundle according to the first embodiment.
Figure 3:
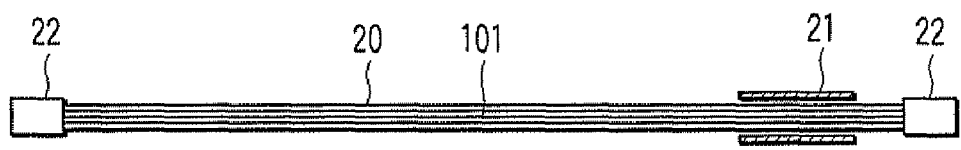
FIG. 3 is a partly cross-sectional side view showing the state in which fiber bundle fixing jigs are mounted on both end portions of the fiber bundle shown in FIG. 2.

Next, a description is given of an optical fiber bundle manufacturing method for manufacturing the first optical fiber bundle 11 on the insertion section 8 side of the endoscope 1 and the second optical fiber bundle 12 on the flexible tube 7 side, which are light guides of the endoscope system according to the present embodiment. To start with, in a pre-process step, as shown in FIG. 2, a plurality of optical fibers 101, each having a predetermined length and a fiber diameter of, e.g. 30μ, are bundled to form a fiber bundle 20 having a bundle diameter of 3.2 mm. Then, a mouthpiece 21 is fitted on one end portion of the fiber bundle 20. Thereafter, fiber bundle fixing jigs 22 are mounted on both end portions of the fiber bundle 20 (see FIG. 3).

Figure 4:
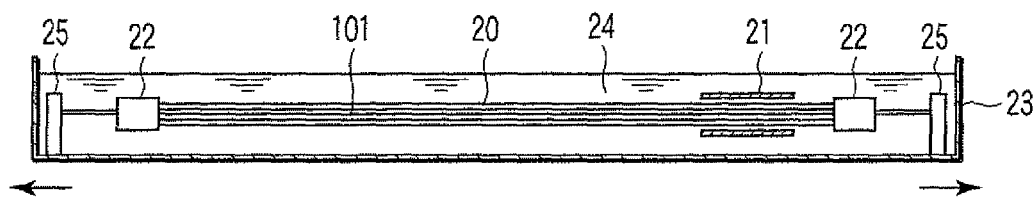
FIG. 4 is a partly cross-sectional side view showing a work of fixing the fiber bundle shown in FIG. 3 on fixing bases in the state in which the fiber bundle is immersed and stretched in an ethanol bath.
Figure 5:
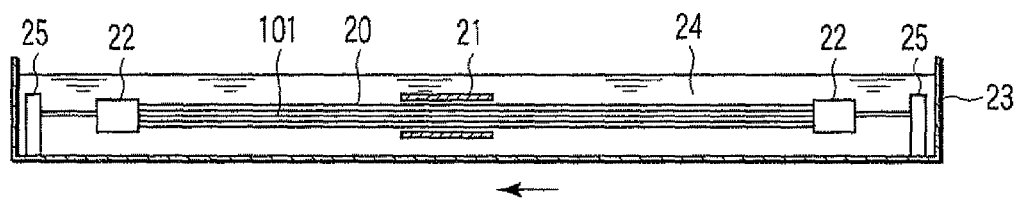
FIG. 5 is a partly cross-sectional side view showing a work of moving the mouthpiece to a position of division in the state in which the fiber bundle immersed in the ethanol bath is fixed on the fixing bases.

Subsequently, an immersion step begins. As shown in FIG. 4, the fiber bundle 20 is immersed in ethanol 24 in an ethanol bath 23 in which ethanol is stored. Fixing bases 25 are provided at both end portions in the ethanol bath 23. The fiber bundle fixing jig 22 at one end portion of the fiber bundle 20 is fixed to one fixing base 25. Then, the other end portion of the fiber bundle 20 is pulled and fixed to the other fixing base 25 in the state in which the fiber bundle 20 is stretched in a rod shape. After the fiber bundle 20 is fixed, the mouthpiece 21 is moved to a position of division (division part) of the fiber bundle 20, as shown in FIG. 5.

Figure 6:
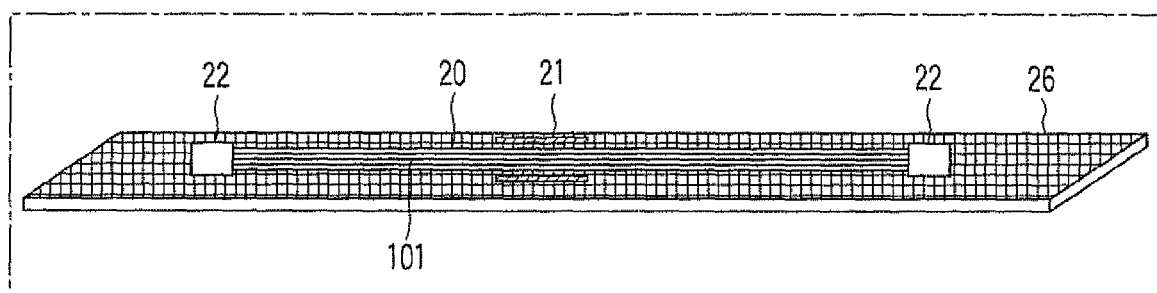
FIG. 6 is a view showing a work of drying the fiber bundle which is impregnated with ethanol, and evaporating the ethanol component.

Then, a fiber bundle division step begins. The fiber bundle 20 is removed from the fixing bases 25, and the fiber bundle 20 is taken out of the ethanol bath 23. As shown in FIG. 6, the fiber bundle 20, which is taken out, is placed on a drying net 26 and is dried. At this time, in order to make drying faster, the fiber bundle 20 is kept, for example, in a vacuum drying furnace 26a for about 20 minutes, and the component of ethanol 24 is evaporated and dried.

Figure 7:
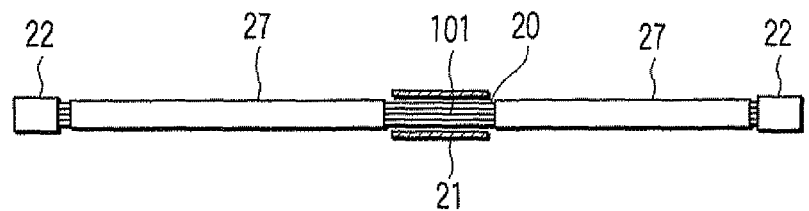
FIG. 7 is a partly cross-sectional side view for explaining a work of coating breakage-prevention resin tubes on outer peripheral parts on both sides of the mouthpiece disposed at the position of division of the dried fiber bundle.

Subsequently, as shown in FIG. 7, for example, resin tubes 27 for preventing breakage, such as silicone tubes, are coated on the outer periphery of the fiber bundle 20. At this time, the breakage-prevention resin tubes 27 are coated on parts other than the mouthpiece 21, that is, on the outer peripheral surfaces of the fiber bundle 20 on both sides of the mouthpiece 21.

Figure 8A:
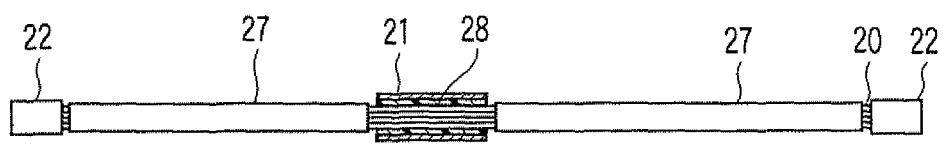
FIG. 8A is a partly cross-sectional side view showing a work of bonding and fixing the mouthpiece that is fitted on the fiber bundle on which the resin tubes are coated.
Figure 8B:
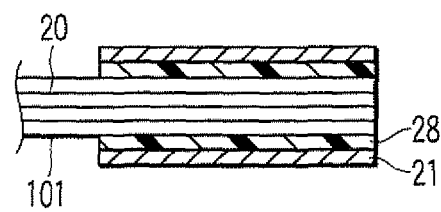
FIG. 8B is an enlarged longitudinal cross-sectional view of the main part in FIG. 8A.

As shown in FIG. 8A and FIG. 8B, for example, a heat-resistant adhesive 28 is coated on the division part of the fiber bundle 20, and the mouthpiece 21 on the fiber bundle 20 is bonded and fixed by means of the heat-resistant adhesive.

Figure 9:
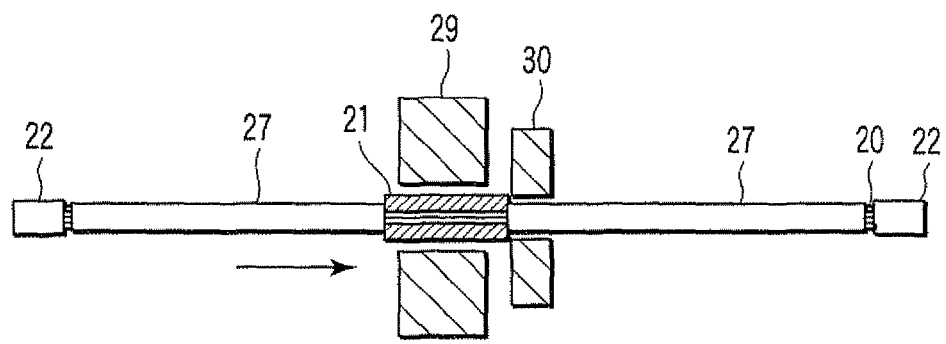
FIG. 9 shows a work of fusing and fixing the mouthpiece that is fitted on the fiber bundle on which the resin tubes are coated.
Figure 10:
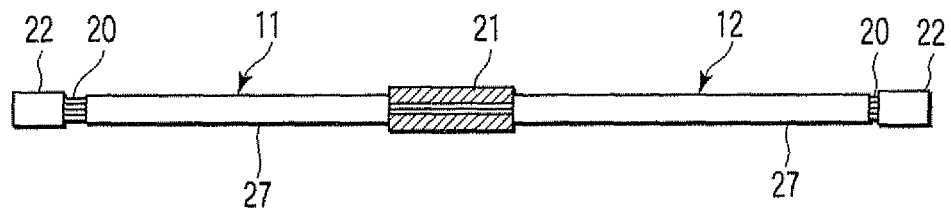
FIG. 10 shows a state in which the mouthpiece is fused and fixed on the fiber bundle.

There is another method of fixing the mouthpiece 21 on the fiber bundle 20. For example, as shown in FIG. 9, the mouthpiece 21 at the division part is heated and fused by a well-known drying furnace 29. Then, using a diameter-reducing die 30, the diameter of the fused mouthpiece 21 is reduced and the mouthpiece 21 is fixed, as shown in FIG. 10.

Figure 11:
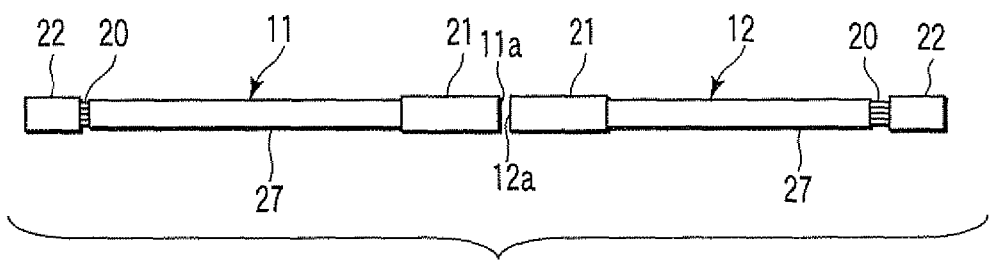
FIG. 11 shows a state in which the mouthpiece, after fixed on the fiber bundle, is cut at the position of division.

Subsequently, the fiber bundle 20 is cut by a cutting machine (not shown) at a predetermined division position on the mouthpiece 21, and divided into two (first and second) optical fiber bundles 11 and 12, as shown in FIG. 11. Further, division surfaces 11a and 11b of the first and second optical fiber bundles 11 and 12 are polished and processed, and end faces having the same properties and condition are formed.

Figure 12A:
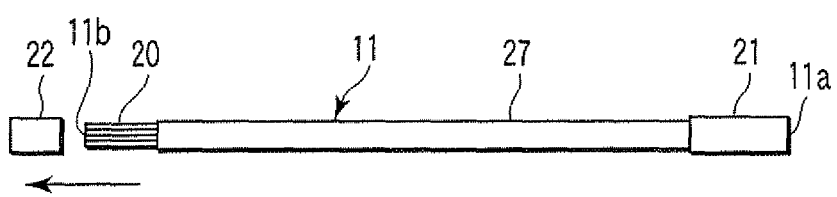
FIG. 12A shows a work of separating a fiber bundle fixing jig from the end portion of a first optical fiber bundle which is divided in FIG. 11.
Figure 13A:
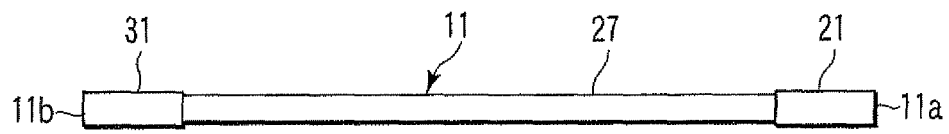
FIG. 13A shows a state in which a fixing mouthpiece is attached to the end portion of the first optical fiber bundle, from which the fiber bundle fixing jig is separated in FIG. 12A.

Thereafter, as shown in FIG. 12A, the fiber bundle fixing jig 22, which is attached to an end face 11b opposite to the division surface 11a of the first optical fiber bundle 11, is removed. Then, as shown in FIG. 13A, a fixing mouthpiece 31, in place of the fiber bundle fixing jig 22, is fixed by, for example, a heat-resistant adhesive, to the end face 11b of the first optical fiber bundle 11, from which the fiber bundle fixing jig 22 has been removed. The end face 11b on the fixing mouthpiece 31 side of the first optical fiber 11 is ground and polished, and the fabrication of the first optical fiber bundle 11 is completed.

Figure 12B:
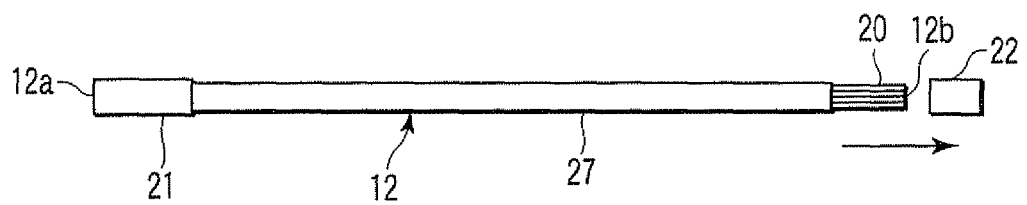
FIG. 12B shows a work of separating a fiber bundle fixing jig from the end portion of a second optical fiber bundle which is divided in FIG. 11.
Figure 13B:
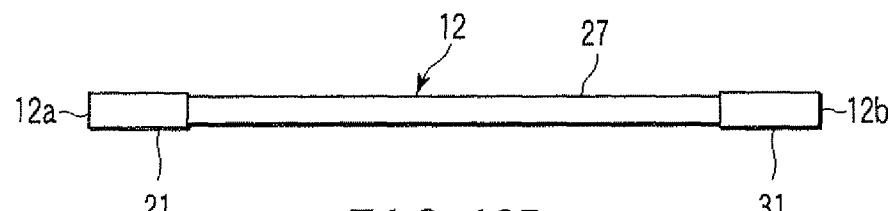
FIG. 13B shows a state in which a fixing mouthpiece is attached to the end portion of the second optical fiber bundle, from which the fiber bundle fixing jig is separated in FIG. 12B.

Similarly, as shown in FIG. 12B, the fiber bundle fixing jig 22, which is attached to an end face 12b opposite to the division surface 12a of the second optical fiber bundle 12, is removed. Then, as shown in FIG. 13B, a fixing mouthpiece 31, in place of the fiber bundle fixing jig 22, is fixed by, for example, a heat-resistant adhesive, to the end face 12b of the second optical fiber bundle 12, from which the fiber bundle fixing jig 22 has been removed. The end face 12b on the fixing mouthpiece 31 side of the second optical fiber 12 is ground and polished, and the fabrication of the second optical fiber bundle 12 is completed. Thereby, the fiber bundle division step is completed.

The fabricated two (first and second) optical fiber bundles 11 and 12 are formed by cutting and dividing the single fiber bundle 20 at an intermediate part thereof. Thus, the first and second optical fiber bundles 11 and 12 have outer end portions corresponding to both end portions of the optical fiber bundle 20 prior to the division, and inner end portions corresponding to the division surfaces 11a and 12a.

The first optical fiber bundle 11 of this embodiment, which is manufactured by the above-described optical fiber bundle manufacturing method, is assembled in the insertion section 8 of the endoscope 1. Similarly, the second optical fiber bundle 12 is assembled in the flexible tube 7.

The end face 11b, which is opposite to the division surface 11a of the first optical fiber bundle 11, is coupled to the distal end side of the insertion section 8 of the endoscope 1, and the end portion on the division surface 11a side is optically coupled to the flexible tube connection section 91 of the operation section 9. On the other hand, the end face 12b, which is opposite to the division surface 12a of the second optical fiber bundle 12, is connected to the external connection section 72 of the flexible tube 7, which is connected to the external light source, and the end portion on the division surface 12a side of the second optical fiber bundle 12 is connected to the endoscope connection section 71 of the flexible tube 7. If the endoscope connection section 71 of the flexible tube 7 is connected to the flexible tube connection section 91 of the operation section 9, the division surface 12a of the second optical fiber bundle 12 is set to be opposed to the division surface 11a of the first optical fiber bundle 11, which is disposed in the flexible tube connection section 91 of the operation section 9.

Thereby, a light transmission path is cooperatively formed in the state in which illumination light from the external light source is guided from the second optical fiber bundle 12 to the first optical fiber bundle 11 via the endoscope connection section 71 of the flexible tube 7 and the flexible tube connection section 91 of the operation section 9.

With the above-described structure, the following advantageous effects can be obtained. Specifically, in the present embodiment, the optical fiber bundle 10, which is formed by bundling a plurality of optical fibers 101, is cut at the part of the mouthpiece 21 fixed on the intermediate part of the optical fiber bundle 10, thereby forming two divided first and second optical fiber bundles 11 and 12. Then, the first optical fiber bundle 11 is assembled in the insertion section 8 of the endoscope 1, and the second optical fiber bundle 12 is assembled in the flexible tube 7, and thus the first light guide within the insertion section 8 of the endoscope 1 and the second light guide within the flexible tube 7 are formed. Thereby, a separable light transmission path of the light guide is constituted. According to this structure, the division surfaces 11a and 12a of the first and second optical fiber bundles 11 and 12 are formed of the fiber bundle 20 that is composed by bundling the same optical fibers 101, and thus have the same properties and condition. Hence, even in the case where the light transmission path is formed by detachably disposing the division surfaces 11a and 11b such that the division surfaces 11a and 11b are opposed to each other, the light amount loss between the coupled division surfaces 11a and 11b at the time of light transmission can be minimized. As a result, at the connection part between the flexible tube connection section 91 of the operation section 9 of the endoscope system and the endoscope connection section 71 of the flexible tube 7, the end face of the second optical fiber bundle 12 on the flexible tube 7 side and the end face of the first optical fiber bundle 11 on the operation section 9 side are configured to be optically coupled. By this structure, even in the case where the separable light transmission path of the light guide is formed, light transmission with high efficiency can be realized.

Specifically, in the case where the separable light transmission path of the light guide in the endoscope system is formed by using the first and second optical fiber bundles 11 and 12 that are formed by attaching and fixing the mouthpiece 21 on the fiber bundle 20, it has been confirmed by experiments that the light amount at the time of illumination is 70%, which is less by about 30% than the light amount of 100% at the time of illumination by the non-separated single optical fiber bundle 20.

Further, in the case where the light guide in the endoscope system is formed by using the first and second optical fiber bundles 11 and 12 that are formed by fusing and fixing the mouthpiece 21 on the fiber bundle 20, it has been confirmed by experiments that the light amount is 80%, which is less by about 20% than the light amount of 100% with the non-separated single optical fiber bundle 20.

By contrast, in the case where the separable light transmission path of the light guide in a similar endoscope system is formed by using two separate optical fiber bundles as in the prior art, it has been confirmed by experiments that the light amount decreases by 40% and becomes 60%. It is confirmed by this experimental result that the light transmission efficiency can be enhanced by the first and second optical fiber bundles 11 and 12 of the present embodiment, compared to the conventional optical fiber bundles.

In addition, in the method of manufacturing the above-described fiber bundle, a plurality of optical fibers 101 are first bundled, and the fiber bundle 20 is formed and inserted in the mouthpiece 21. Then, the fiber bundle 20 is immersed in the ethanol 24, stretched, and dried, and thus the ethanol 24 is evaporated. Subsequently, the resin tubes 27 are coated on the fiber bundle 20. After the mouthpiece 21 is fixed on the fiber bundle 20, the fiber bundle 20 is cut at the part of the mouthpiece 21. Thus, the division surfaces 11a and 12a of the first and second optical fiber bundles 11 and 12 are formed.

According to this method, the division surfaces 11a and 11b of the first and second optical fiber bundles 11 and 12, which have the same end-surface properties and condition, can easily and simply be formed. Therefore, this method contributes to formation of a separable light transmission path with less light amount loss. For example, a high-efficiency light transmission path, which is separable in the light guide of the endoscope system, can easily be formed.

The present invention is not limited to the above-described embodiment. For example, as shown in embodiments that are described below, alignment means may be provided on the mouthpiece 21 of the fiber bundle 20 prior to cutting. Thereby, in the case where the first and second optical fiber bundles 11 and 12 are assembled in the insertion section 8 of the endoscope 1 and the flexible tube 7 and the separable light transmission path of the light guide in the endoscope system is formed, the alignment work with higher precision can be realized. In the embodiments to be described below, the parts common to those in the above-described embodiment (FIG. 1 to FIG. 13) are denoted by like reference numerals, and a detailed description is omitted.

Figure 14:
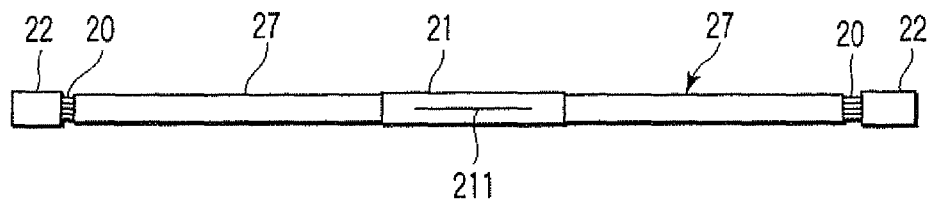
FIG. 14 shows a state before an optical fiber bundle according to a second embodiment of the invention is cut and divided.
Figure 15:
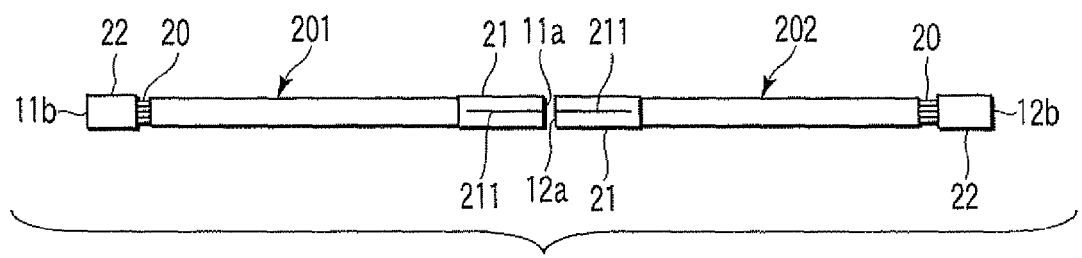
FIG. 15 shows a state in which the optical fiber bundle shown in FIG. 14 is cut and divided.

FIG. 14 and FIG. 15 show a second embodiment of the present invention. In this embodiment, as shown in FIG. 14, a straight mark line 211 is axially provided as alignment means on the outer peripheral part of the mouthpiece 21, which is to be cut and divided, of the fiber bundle 20 prior to cutting. Then, the fiber bundle 20 is cut and divided at the part of the mouthpiece 21, and the first and second optical fiber bundles 11 and 12 are formed. Thereafter, the first and second optical fiber bundles 11 and 12 are assembled in the insertion section 8 of the endoscope 1 and the flexible tube 7. At this time, the end portion of the first optical fiber bundle 11, which is located on the division surface 11a side, is connected to the flexible tube connection portion 91 of the operation section 9, and the end portion of the second optical fiber bundle 12, which is located on the division surface 12a side, is connected to the endoscope connection section 71 of the flexible tube 7.

When the endoscope connection section 71 of the flexible tube 7 is connected to the flexible tube connection section 91 of the operation section 9, the mark line 211 on the mouthpiece 21 provided on the periphery of the division surface 12a of the second optical fiber bundle 12 is aligned with the mark line 211 on the mouthpiece 21 provided on the periphery of the division surface 11a of the first optical fiber bundle 11. Thereby, the division surfaces 11a and 12a of the first and second optical fiber bundles 11 and 12, which have the same end-surface properties and condition, can precisely be aligned.

FIG. 16 shows a third embodiment of the present invention. In this embodiment, an alignment V groove 212, which extends over the division part of the mouthpiece 21, is provided as alignment means on the outer periphery of the mouthpiece 21 of the fiber bundle 20 prior to cutting.

When the endoscope connection section 71 of the flexible tube 7 is connected to the flexible tube connection section 91 of the operation section 9, the V groove 212 on the mouthpiece 21 provided on the periphery of the division surface 12a of the second optical fiber bundle 12 is aligned with the V groove 212 on the mouthpiece 21 provided on the periphery of the division surface 11a of the first optical fiber bundle 11. Thereby, the division surfaces 11a and 12a of the first and second optical fiber bundles 11 and 12, which have the same end-surface properties and condition, can precisely be aligned.

FIG. 17 shows a fourth embodiment of the present invention. In this embodiment, an alignment U groove 213, which extends over the division part of the mouthpiece 21, is provided as alignment means on the outer periphery of the mouthpiece 21 of the fiber bundle 20 prior to cutting.

When the endoscope connection section 71 of the flexible tube 7 is connected to the flexible tube connection section 91 of the operation section 9, the U groove 213 on the mouthpiece 21 provided on the periphery of the division surface 12a of the second optical fiber bundle 12 is aligned with the U groove 213 on the mouthpiece 21 provided on the periphery of the division surface 11a of the first optical fiber bundle 11. Thereby, the division surfaces 11a and 12a of the first and second optical fiber bundles 11 and 12, which have the same end-surface properties and condition, can precisely be aligned.

The alignment grooves are not limited to the V groove 212 shown in FIG. 16 and the U groove 213 shown in FIG. 17, and grooves with other various shapes may be formed.

Figure 19:
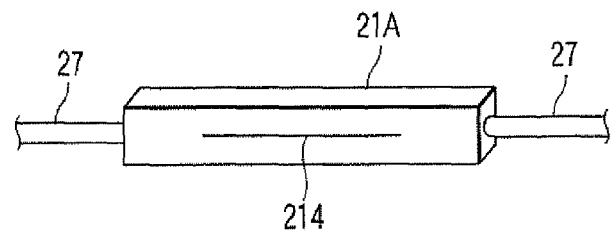
FIG. 19 shows a mouthpiece with a reduced diameter of the optical fiber bundle according to the fifth embodiment.
Figure 20:
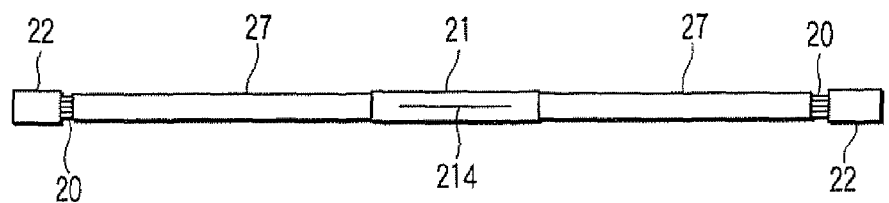
FIG. 20 is a view showing the optical fiber bundle according to the fifth embodiment, which has been subjected to a diameter-reducing work.
Figure 21:
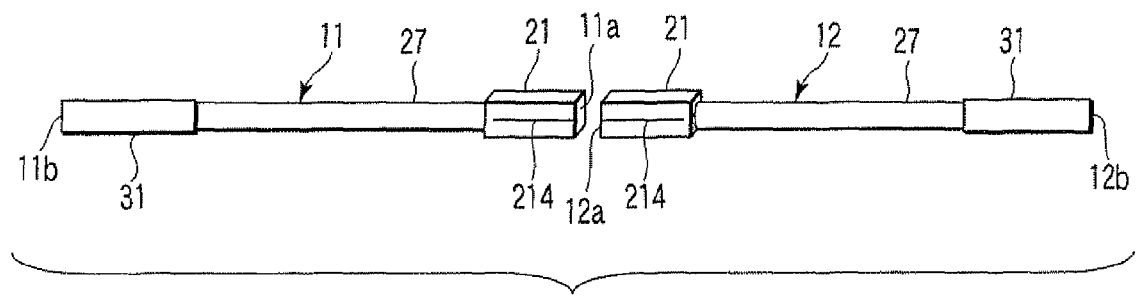
FIG. 21 is a view showing a state in which the optical fiber bundle according to the fifth embodiment, after subjected to the diameter-reducing work, is cut into a first optical fiber bundle and a second optical fiber bundle.

FIG. 18 to FIG. 21 show a fifth embodiment of the present invention. In this embodiment, when the mouthpiece 21 that is mounted on the intermediate part of the fiber bundle 20 prior to cutting is fused and fixed, a mouthpiece 21A with a rectangular cross section, as shown in FIG. 19, is formed as alignment means.

In this embodiment, a diameter-reducing die 32A, which is formed by a mold having a cavity C with a rectangular cross-sectional shape, is used as the diameter-reducing die 32 that is used in the apparatus shown in FIG. 9. As shown in FIG. 18, like the case of FIG. 9, the mouthpiece 21 at the division part of the fiber bundle 20 prior to cutting is heated and fused by the heating furnace 29. Then, the diameter of the fused mouthpiece 21 is reduced by using the diameter-reducing die 30A. At this time, by reducing the diameter of the mouthpiece 21 in the fused state by the diameter-reducing die 30A, the mouthpiece 21 in the fused state is diameter-reduced to have a rectangular cross-sectional shape, as shown in FIG. 19. Thus, the mouthpiece 21A with a rectangular cross-sectional shape is formed.

Subsequently, the fiber bundle 20 is cut and divided at the part of the mouthpiece 21A with the rectangular shape, and the first and second optical fiber bundles 11 and 12 are formed. Thereafter, the first and second optical fiber bundles 11 and 12 are assembled in the insertion section 8 of the endoscope 1 and the flexible tube 7. At this time, the end portion of the first optical fiber bundle 11, which is located on the division surface 11a side, is connected to the flexible tube connection portion 91 of the operation section 9, and the end portion of the second optical fiber bundle 12, which is located on the division surface 12a side, is connected to the endoscope connection section 71 of the flexible tube 7.

When the endoscope connection section 71 of the flexible tube 7 is connected to the flexible tube connection section 91 of the operation section 9, the outer shape of the rectangular mouthpiece 21A provided on the periphery of the division surface 12a of the second optical fiber bundle 12 is aligned with the outer shape of the rectangular mouthpiece 21A provided on the periphery of the division surface 11a of the first optical fiber bundle 11. Thereby, the division surfaces 11a and 12a of the first and second optical fiber bundles 11 and 12, which have the same end-surface properties and condition, can precisely be aligned.

As described above, even in the alignment means with the rectangular mouthpiece 21A, a straight mark line 214, which extends over the division surfaces, may axially be provided, as shown in FIG. 19, on the outer peripheral part of the rectangular mouthpiece 21A. In this case, when the endoscope connection section 71 of the flexible tube 7 is connected to the flexible tube connection section 91 of the operation section 9, the mark line 214 on the rectangular mouthpiece 21A provided on the periphery of the division surface 12a of the second optical fiber bundle 12 is aligned with the mark line 214 on the mouthpiece 21 provided on the periphery of the division surface 11a of the first optical fiber bundle 11. Thereby, a better advantageous effect can be obtained. Instead of the mark line 214, the above-described V groove 212 or U groove 213 may be formed on the outer periphery of the rectangular mouthpiece 21A.

The outer shape of the mouthpiece 21 is not limited to that of the rectangular mouthpiece 21A. For example, as in a sixth embodiment of the invention shown in FIG. 22, a mouthpiece 21 having a triangular cross-sectional shape may be formed by using, as the diameter-reducing die 32, a diameter-reducing die 321 which is formed by a mold having a cavity C2 with a rectangular cross-sectional shape. Alternatively, as in a seventh embodiment of the invention shown in FIG. 23, a mouthpiece 21 having a hexagonal cross-sectional shape may be formed by using, as the diameter-reducing die 32, a hexagonal diameter-reducing die 322 which is formed by a mold having a cavity C3 with a hexagonal cross-sectional shape. Alternatively, mouthpieces with other polygonal cross-sectional shapes may be formed. In these cases, too, the same advantageous effect as with the mouthpiece 21A with the rectangular cross-sectional shape can be obtained.

In the above-described embodiments, the fiber bundle 20 is cut at one part and divided into the first and second optical fiber bundles 11 and 12. Alternatively, the optical fiber bundle may be cut at two or more parts and divided into three or more optical fiber bundles having the same end-face properties and condition of the division surface.

The present invention is not limited to the above-described embodiments. At the stage of practicing the invention, various modifications may be made without departing from the spirit of the invention. Further, the embodiments include various inventions at various stages, and various inventions may be derived by properly combining structural elements disclosed in the embodiments.

For example, even if some structural elements are omitted from all the structural elements disclosed in the embodiments, structures from which these structural elements are omitted may be derived as inventions in the case where the object of the invention and the advantageous effects, which are described in the specification, can be achieved.

According to the above-described embodiments of the invention, the following structures can be obtained.

(Item 1)
An optical fiber bundle characterized in that first and second optical fiber bundles, which are obtained by dividing a bundle of a plurality of optical fibers at an intermediate part of the bundle, are optically coupled by opposing division surfaces of the first and second optical fiber bundles to each other.

(Item 2)
The optical fiber bundle according to item 1, characterized in that one of divided mouthpieces is provided on a division part of each of the first and second optical fiber bundles.

(Item 3)
The optical fiber bundle according to item 2, characterized in that alignment means is provided on the mouthpiece in accordance with at least the division part.

(Item 4)
The optical fiber bundle according to any one of items 1 to 3, characterized in that the first and second optical fiber bundles form light guides.

(Item 5)
The optical fiber bundle according to any one of items 1 to 4, characterized in that the first and second optical fiber bundles are coated with resin tubes.

(Item 6)
A method of manufacturing an optical fiber bundle, characterized by comprising:
a pre-process step of inserting an optical fiber bundle of a plurality of optical fibers into a division mouthpiece, and attaching fiber bundle fixing jigs on both end portions of the optical fiber bundle;
an immersion step of immersing the optical fiber bundle, on which the fiber bundle fixing jigs are attached, in ethanol, stretching the optical fiber bundle, and positioning the division mouthpiece at a division part of the optical fiber bundle; and
a fiber bundle division step of drying the optical fiber bundle that is immersed in the ethanol in the immersion step, evaporating the ethanol, fixing the division mouthpiece, cutting the optical fiber bundle at the division mouthpiece, separating the fiber bundle fixing jigs, fixing mouthpieces on end portions, and forming first and second optical fiber bundles.

(Item 7)
The method of manufacturing an optical fiber bundle, according to item 6, characterized in that in the fiber bundle division step, the optical fiber bundle, which is immersed in the ethanol in the immersion step, is dried and ethanol is evaporated, resin tubes are coated on the optical fiber bundle, the division mouthpiece is fixed, the fiber bundle is cut at the division mouthpiece, the fiber bundle fixing jigs are separated, mouthpieces are fixed on end portions, and first and second optical fiber bundles are formed.

(Item 8)
The method of manufacturing an optical fiber bundle, according to items 6 or 7, characterized in that the first and second optical fiber bundles are disposed such that the division mouthpieces are opposed, and thus a light path is formed.

(Item 9)
The method of manufacturing an optical fiber bundle, according to any one of items 6 to 8, characterized in that alignment means is provided on the division mouthpiece.

What is claimed is:
1. An endoscope comprising:
an operation section including a light guide cable connection section, and a first divisional fiber bundle unit with a first division surface disposed in the light guide cable connection section;
a light guide cable including an endoscope connection section configured to be connected to the light guide cable connection section, and a second divisional fiber bundle unit with a second division surface disposed in the endoscope connection section, and
wherein the first and the second divisional fiber bundle unit are one and other divided part, respectively, of a fiber bundle unit including a fiber bundle in which a plurality of optical fibers is bundled and which includes a fixing portion in which the plurality of optical fibers are fixed, and a bundling member provided on the fixing portion and provided with a straight alignment portion extending in an axial direction of the fiber bundle, the fiber bundle unit cut at the alignment portion, and the first and the second division surface are one and other cut surface of the fiber bundle unit, respectively, and
the first and the second divisional fiber bundle unit are assembled in the operation section and the light guide cable, respectively, such that the first and the second division surface are opposed to each other and one and other divided part of the alignment portion are aligned with each other when the endoscope connection section is connected to the light guide cable connection section.

2. The endoscope according to claim 1, wherein the alignment portion includes one of a mark line, a V groove and a U groove.

3. A method of manufacturing an endoscope comprising:
providing a fiber bundle in which a plurality of optical fibers is bundled;
providing a bundling member provided with a straight alignment portion;
fixing the plurality of optical fibers in a part of the fiber bundle to form a fixing portion;
providing the fixing portion with the bundling member such that the alignment portion extends in an axial direction of the fiber bundle to form a fiber bundle unit;
cutting the fiber bundle unit at the alignment portion to form one and other divisional fiber bundle unit: and
assembling the one and the other divisional fiber bundle unit in an operation section and an light guide cable of an endoscope, respectively, and
wherein the assembling includes disposing one and other cut surface of the fiber bundle unit in a light guide cable connection section of the operation section and an endoscope connection section of the light guide cable, respectively, such that the one and the other cut surface are opposed to each other and one and other divided part of the alignment portion are aligned with each other when the endoscope connection section is connected to the light guide cable connection section.

* * * * *